US007168103B2

(12) United States Patent
Aldridge et al.

(10) Patent No.: US 7,168,103 B2
(45) Date of Patent: Jan. 30, 2007

(54) HEIGHT ADJUSTABLE PROTECTIVE GARMENT

(75) Inventors: Donald Aldridge, New Carlisle, OH (US); John Granby, Centerville, OH (US); Harry P. Winer, Holliston, MA (US)

(73) Assignee: Lion Apparel, Inc., Dayton, OH (US)

(*) Notice: Subject to any disclaimer, the term of this patent is extended or adjusted under 35 U.S.C. 154(b) by 103 days.

(21) Appl. No.: 10/749,758

(22) Filed: Dec. 31, 2003

(65) Prior Publication Data

US 2005/0144694 A1 Jul. 7, 2005

(51) Int. Cl.
*A61B 17/00* (2006.01)

(52) U.S. Cl. .................................................. 2/458; 2/69

(58) Field of Classification Search ............ 2/455–458, 2/2.16, 2.17, 69, 81, 84–87, 93, 94, 96, 97, 2/100, 108, 75, 80, 111, 227, 235–237, 269, 2/71, 72

See application file for complete search history.

(56) References Cited

U.S. PATENT DOCUMENTS

| | | | | | |
|---|---|---|---|---|---|
| 57,950 | A | * | 9/1866 | Moody | 2/217 |
| 964,697 | A | * | 7/1910 | Rogers | 2/407 |
| 1,137,659 | A | | 4/1915 | Oilar | |
| 2,507,463 | A | * | 5/1950 | Smith | 2/76 |
| 2,675,554 | A | * | 4/1954 | Gertz | 2/80 |
| 2,725,565 | A | * | 12/1955 | Wyner | 2/70 |
| 3,947,896 | A | * | 4/1976 | Taylor | 2/217 |
| 4,275,513 | A | * | 6/1981 | Antonious | 36/50.1 |
| 4,310,926 | A | * | 1/1982 | Maroist | 2/81 |
| 4,475,252 | A | * | 10/1984 | Peyser et al. | 2/125 |
| 4,573,218 | A | * | 3/1986 | Saggs | 2/93 |
| 4,658,442 | A | * | 4/1987 | Tomlinson et al. | 2/94 |
| 4,773,101 | A | * | 9/1988 | Kapp et al. | 2/69.5 |
| 4,888,830 | A | * | 12/1989 | Putnam | 2/327 |
| 4,985,936 | A | | 1/1991 | Jones | |
| 5,095,549 | A | * | 3/1992 | Aldridge | 2/304 |
| 5,163,183 | A | * | 11/1992 | Smith | 2/81 |
| 5,274,850 | A | | 1/1994 | Aldridge | |
| 5,331,685 | A | | 7/1994 | Belgard | |
| 5,367,709 | A | * | 11/1994 | Teasley | 2/69 |
| 5,426,787 | A | * | 6/1995 | Freeman | 2/69 |
| 5,539,932 | A | | 7/1996 | Howard | |
| 5,575,010 | A | | 11/1996 | Chung | |
| 5,575,011 | A | * | 11/1996 | Allen | 2/227 |
| 5,640,718 | A | * | 6/1997 | Aldridge | 2/81 |
| 5,692,239 | A | * | 12/1997 | Lewis | 2/125 |

(Continued)

FOREIGN PATENT DOCUMENTS

| | | |
|---|---|---|
| DE | 29817678 | 12/1998 |

(Continued)

*Primary Examiner*—Alissa Hoey
(74) *Attorney, Agent, or Firm*—Thompson Hine LLP

(57) ABSTRACT

A height adjustable protective garment including an outer shell shaped to fit about the chest, torso and legs of a wearer and having a waist portion shaped to be located at or adjacent to a waist of a wearer. The garment further includes an adjusting strip having an attachment portion directly or indirectly coupled to the outer shell and a free end which is generally spaced apart from the attachment portion. The free end is releasably attachable to the outer shell or to the strip of material to adjust the height of the protective garment, and the adjusting strip is located at or adjacent to the waist portion.

28 Claims, 7 Drawing Sheets

U.S. PATENT DOCUMENTS 5,787,511 A * 8/1998 Garside .......................... 2/269
5,860,162 A * 1/1999 Love ............................ 2/2.14
5,860,163 A * 1/1999 Aldridge .......................... 2/81
5,884,332 A * 3/1999 Snedeker .......................... 2/97
5,915,535 A * 6/1999 Henrekin-Jordan ......... 2/195.2
5,960,473 A 10/1999 Tajima
5,996,122 A 12/1999 Aldridge et al.
6,038,700 A 3/2000 Aldridge et al.
6,049,906 A * 4/2000 Aldridge .......................... 2/23
6,058,508 A 5/2000 Brown Honeysuckle
6,148,445 A * 11/2000 Spruill .......................... 2/125
6,223,352 B1 * 5/2001 Watlington ...................... 2/80
6,272,691 B1 * 8/2001 Henricksen et al. ........... 2/338
6,374,414 B1 * 4/2002 Collier ............................ 2/69
6,430,754 B1 8/2002 Taylor et al.
6,467,096 B1 * 10/2002 Coluccio .................... 2/195.2
6,610,022 B1 * 8/2003 Ashbaugh et al. ............ 602/19
6,687,913 B2 2/2004 Aldridge
6,694,522 B1 * 2/2004 Neal ............................. 2/114
6,698,031 B2 3/2004 Lewis
6,735,789 B2 * 5/2004 Kelleher et al. ............... 2/458
6,859,944 B2 * 3/2005 Kim .............................. 2/237
6,892,394 B2 * 5/2005 Grilliot et al. ................... 2/81

FOREIGN PATENT DOCUMENTS

| | | |
|---|---|---|
| DE | 20112417 | 10/2001 |
| EP | 0992423 | 4/2000 |
| FR | 2447688 | 8/1980 |
| GB | 238525 | 7/2003 |

* cited by examiner

HEIGHT ADJUSTABLE PROTECTIVE GARMENT

The present invention relates to protective garments and, more particularly, to protective garments having a height that can be adjusted.

BACKGROUND

Protective or hazardous duty garments are widely used in various industries to protect the wearer from various hazardous conditions, such as heat, smoke, cold, sharp objects, chemicals, liquids, fumes and the like. The protective garments should conform to the height of the wearer. In particular, the protective garment should be long enough to ensure complete protection to the wearer, but should not be so long as to present a tripping hazard, provide a "catch" point for equipment, drag on the floor such that it can absorb materials located on the floor, etc. Additionally if the garment is too long the crotch of the garment may be too low which can impede the climbing and walking of the wearer and present durability issues.

Furthermore, a single protective garment may be desired to be worn by wearers of various sizes. Accordingly, there is a need for a protective garment that is height adjustable, and which has a height that can be quickly and easily adjusted.

SUMMARY

In one embodiment, the present invention is a protective garment that has a height or length that can be quickly and easily adjusted. In particular, in one embodiment the invention is a height adjustable protective garment including an outer shell shaped to fit about the chest, torso and legs of a wearer and having a waist portion shaped to be located at or adjacent to a waist of a wearer. The garment further includes an adjusting strip having an attachment portion directly or indirectly coupled to the outer shell and a free end which is generally spaced apart from the attachment portion. The free end is releasably attachable to the outer shell or to the strip of material to adjust the height of the protective garment, and the adjusting strip is located at or adjacent to the waist portion.

In another embodiment the invention is a height adjustable protective garment including an outer shell shaped to fit about the chest, torso and legs of a wearer and being made of abrasion, flame and heat resistant material such that the outer shell can resist igniting, burning, melting, dripping or separation when exposed to a temperature of 500° F. for at least five minutes. The garment further includes a height adjusting system positioned at or adjacent to the waist of the garment such that the height adjusting system can be operated to adjust the height of the protective garment. In yet another embodiment, the height adjusting system includes a first attaching strip extending generally along at least part of the outer shell in a generally closed loop shape and a second attaching strip extending generally along at least part of the outer shell in a generally closed loop shape. The second attaching strip is generally parallel to and spaced apart from the first attaching strip, and the first and second attaching strips are releasably attachable together to adjust the height of the protective garment.

These and other objects and advantages of the present invention will be apparent from the following description, the accompanying drawings and the appended claims.

DETAILED DESCRIPTION

Figure 1:
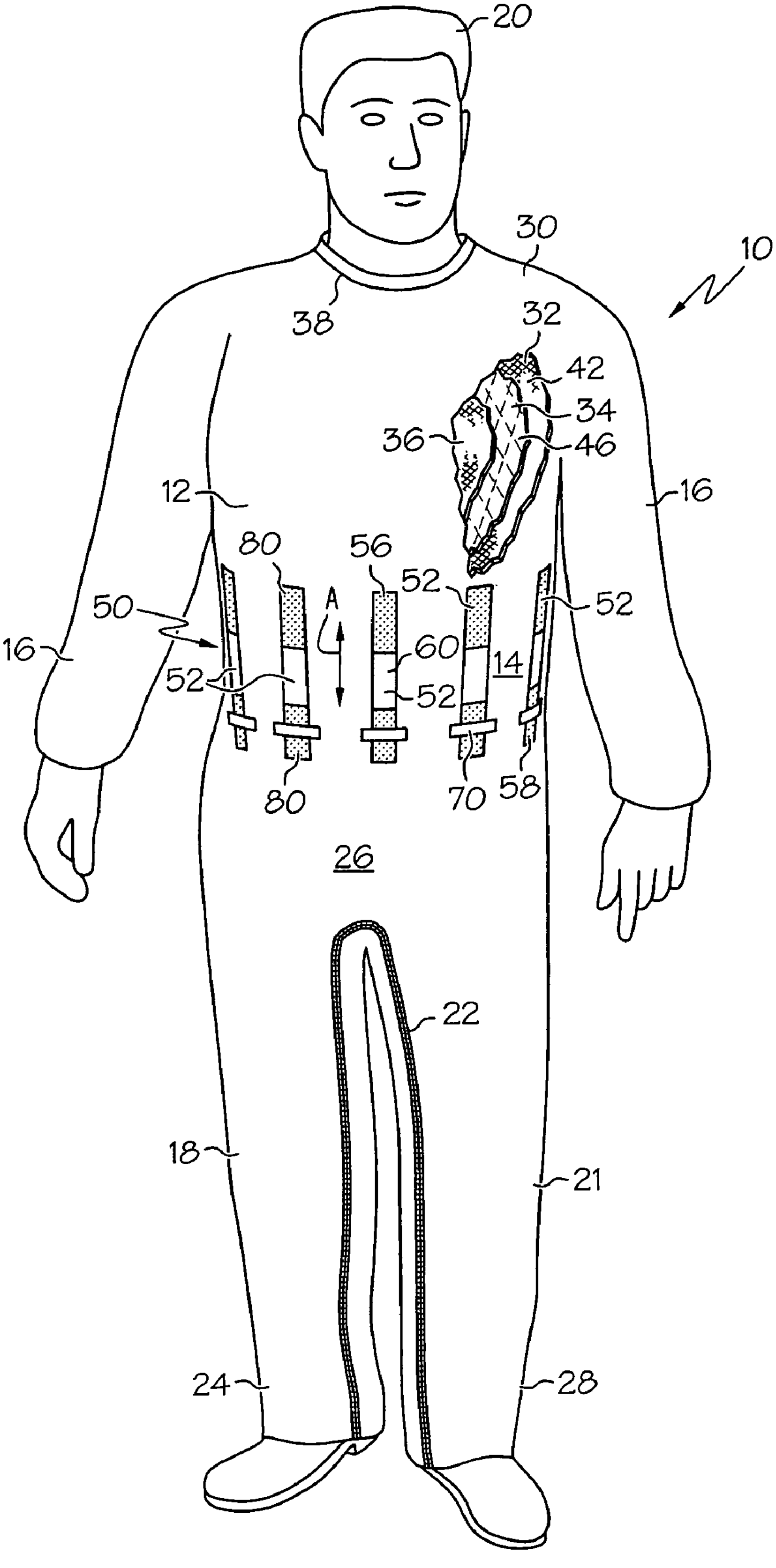
FIG. 1 is a front perspective view of one embodiment of the protective garment of the present invention, shown in a release position, with part of the garment cut away to show the various layers thereof.

FIG. 1 illustrates a protective or hazardous duty garment in the form of a garment or body suit, generally designated 10. The garment 10 may include a torso portion 12 shaped to cover or be located adjacent to the torso of a wearer 20 and waist portion 14 shaped to cover or be located adjacent to the waist of a wearer 20. The garment 10 may also include a pair of arms 16 and a pair of legs 18, 21, shaped to cover or be located adjacent to the arms and legs, respectively, of the wearer 20.

The garment 10 may include a releasable fastener 22 (such as a zipper or the like) which extends from the ankle 24 of leg 18, up and around the crotch 26, and to the ankle 28 of leg 21. The fastener 22 can be opened to fully open the legs 18, 21 so that the garment 10 can be donned doffed by passing the garment 10 over the head and shoulders of a wearer 20. However, the garment 10 may have any of a wide variety of configurations, openings, fasteners (i.e. slide fastener components, snaps, buttons, hook and loop fastening systems (i.e. VELCRO®), straps, ties and the like) in a variety of locations (i.e., across the chest of the garment 10, along the side of the garment 10, etc.) to enable donning and doffing of the garment 10.

Figure 2:
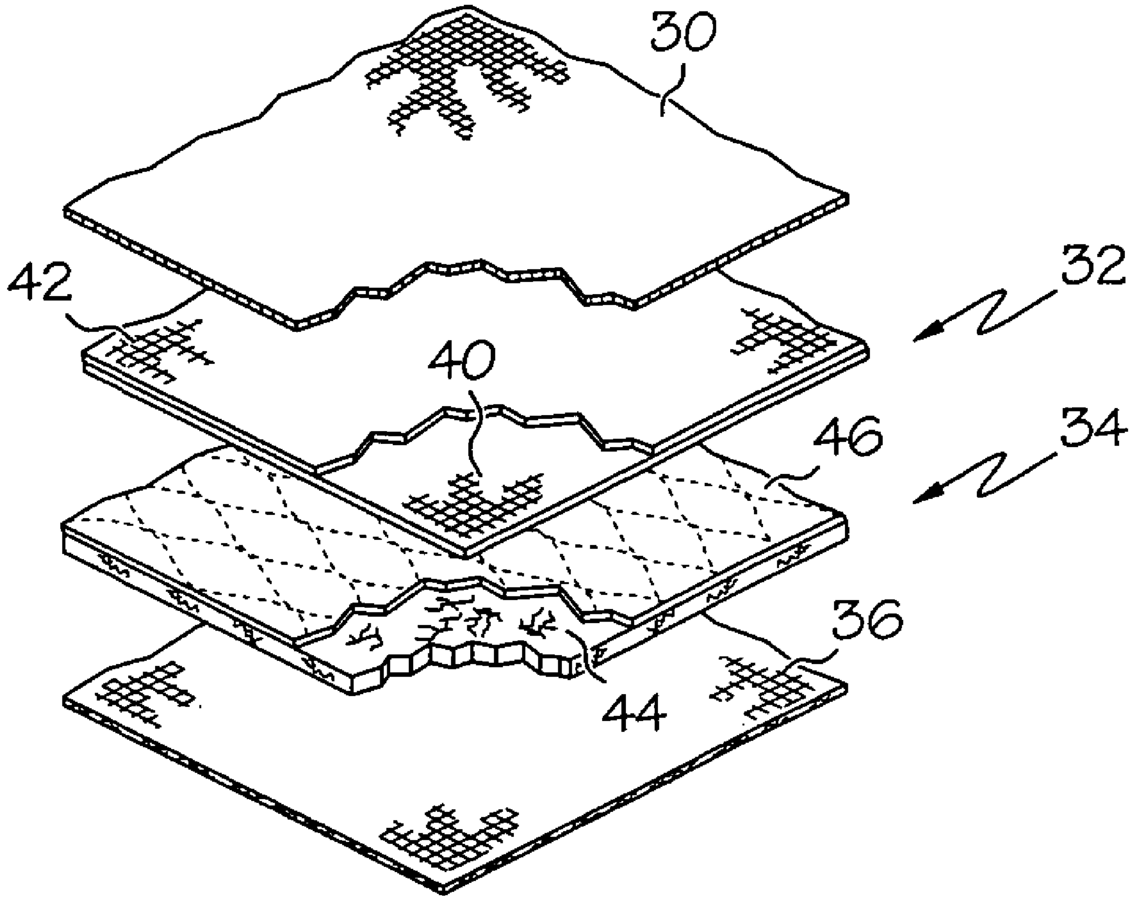
FIG. 2 is a front exploded perspective view illustrating various layers of the garment of FIG. 1.

As shown in FIGS. 1 and 2, the garment 10 may include various layers through the thickness of the garment 10, such as an outer shell 30, a moisture barrier 32 located inside of and adjacent to the outer shell 30, a thermal liner or barrier 34 located inside of and adjacent to the moisture barrier 32, and an inner liner or face cloth 36 located inside of and adjacent to the thermal liner 34. The outer shell 30 may be made of or include a variety of materials, including a flame, heat and abrasion resistant material such as a compact weave of aramid fibers and/or polybenzamidazole fibers. Commercially available aramid materials include NOMEX and KEVLAR fibers (both trademarks of E.I. DuPont de Nemours & Co., Inc.), and commercially available polybenzamidazole fibers including PBI (a trademark of Celanese Corp.) fibers. Thus, the outer shell 30 may be an aramid material, a blend of aramid materials, a polybenzamidazole material, a blend of aramid and polybenzamidazole materials, or other appropriate materials, and may have a weight of, for example, between about 6–10 oz/yd$^2$.

The moisture barrier 32 and thermal liner 34 may be generally coextensive with the outer shell 30, or spaced slightly inwardly from the outer edges (i.e., spaced inwardly from the outer ends of the arms 16, legs 18, 21 and collar 38) of the outer shell 30 to provide moisture and thermal protection throughout the garment 10. The moisture barrier 32 may include a semi-permeable membrane layer 40, which may be generally moisture vapor permeable but generally impermeable to liquid moisture.

The membrane layer 40 may be made of or include expanded polytetrafluoroethylene ("PTFE") such as GORE-TEX or CROSSTECH (both of which are trademarks of W.L. Gore & Associates, Inc.), polyurethane-based materials, neoprene-based materials, cross-linked polymers, polyamid, or other materials. The membrane layer 40 may have microscopic openings that permit moisture vapor to pass therethrough, but block liquids (i.e., water) from passing therethrough. The membrane layer 40 may be made of a microporous material that is either hydrophilic, hydrophobic, or somewhere in between. The membrane layer 40 may also be monolithic and may allow moisture vapor transmission therethrough by molecular diffusion. The membrane layer 40 may also be a combination of microporous and monolithic materials (known as a bicomponent moisture barrier), in which the microporous or monolithic material can be layered or intertwined.

The membrane layer 40 may be bonded or adhered to a substrate 42 of a flame and heat resistant material. The substrate 42 may be aramid fibers similar to the aramid fibers of the outer shell 30, but may be thinner and lighter in weight. The substrate 42 may be woven, non-woven, spunlace or other materials. In the illustrated embodiment, the substrate 42 faces the outer shell 30. However, the orientation of the moisture barrier 32 may be reversed such that the membrane layer 40 faces the outer shell 30.

The thermal liner 34 may be made of any suitable material which provides sufficient thermal insulation. In one embodiment, the thermal liner 34 may include a relatively thick (i.e. typically from 1/16"–3/16" thick) batting, felt or needled non-woven material 44 which can include aramid fiber batting (such as NOMEX batting), aramid needlepunch material, an aramid non-woven material, an aramid blend needlepunch material, an aramid blend batting material, an aramid blend non-woven material, or foam (either open or closed cell) materials. The batting 44 preferably traps air and possesses sufficient loft to provide thermal resistance to the garment 10.

The batting 44 is typically quilted to a thermal liner face cloth 46, and the thermal liner face cloth 46 may be a weave of a lightweight aramid material. Thus, either the batting 44 alone, or the batting 44 in combination with the thermal liner face cloth 46, may be considered to be the thermal liner 34. In one embodiment, the thermal liner 34 may have a thermal protection performance ("TPP") of at least about 20, or of at least about 35. The thermal liner 34 may be treated with a water-resistant material, or may be made of an inherently water-resistant material. In the illustrated embodiment, the thermal liner face cloth 46 faces the moisture barrier 32/outer shell 30. However, the orientation of the thermal liner 34 may be reversed such that the batting 44 faces the moisture barrier 32/outer shell 40.

Although the moisture barrier 32 is shown as being located between the outer shell 30 and the thermal liner 34, the positions of the moisture barrier 32 and thermal liner 34 may be reversed such that the thermal liner 34 is located between the outer shell 30 and the moisture barrier 32.

The face cloth 36 may be the innermost layer of the garment 10 and can provide a comfortable surface for the wearer and protect the batting 44 from abrasion by the wearer. The face cloth 36 may be made of a quilted material as part of a quilt package.

Each layer of the garment 10, and the garment as a whole, may be designed to meet the National Fire Protection Association ("N.F.P.A.") 1971 standards for protective firefighting garments ("Protective Clothing for Structural Firefighting"). The NFPA standards specify various minimum requirements for heat and flame resistance and tear strength. For example, in order to meet the NFPA standards, an outer shell 30 of a garment must be able to resist igniting, burning, melting, dripping and/or separation when exposed to a temperature of 500° F. for at least five minutes. Furthermore, in order to meet the NFPA standards, all combined layers of the garment 10 must provide a thermal protection performance rating of at least thirty five. However, if desired the garment 10 may have a thermal protection performance of less than thirty five, or may not meet various other NFPA standards, in which case the garment 10 may be sold or marketed as not necessarily meeting NFPA standards. For example, the garment 10 may be a recreational snow suit or have various other uses.

Figure 3:
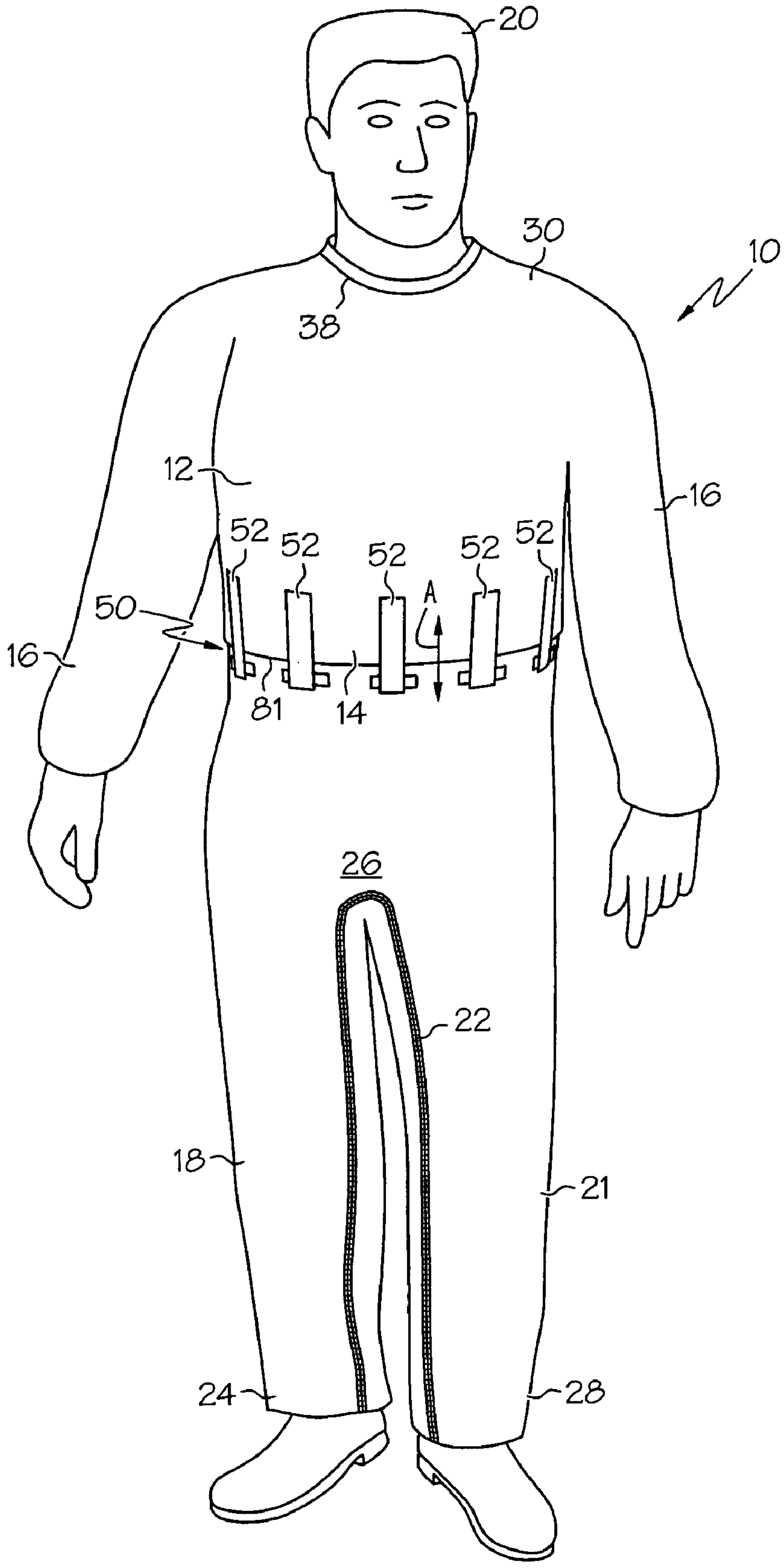
FIG. 3 is a front perspective view of the protective garment of FIG. 1, shown in a drawn-up position.

The garment 10 includes a height adjusting system 50 located on and/or coupled to the outer shell 30 to aid in adjusting the height of the garment 10. In particular, the height adjusting system 50 includes a plurality of adjusting strips 52 spaced about the periphery of the garment 10 at the waist 14 of the garment 10. The garment 10 has a central axis A extending generally perpendicular to the waist 14 of the garment 10 (and along the height or length thereof), and each adjusting strip 52 is oriented generally parallel to the central axis A. For example, as shown in FIGS. 1 and 3, the height adjusting system 50 may include a plurality of adjusting strips 52 equally spaced apart and extending around the periphery of the waist 14 of the garment 10. However, the height adjusting strips 52 may be used in various other locations of the garment 10, including on the arms 16, legs 18, 21, collar 38, etc., as desired.

Figure 4:
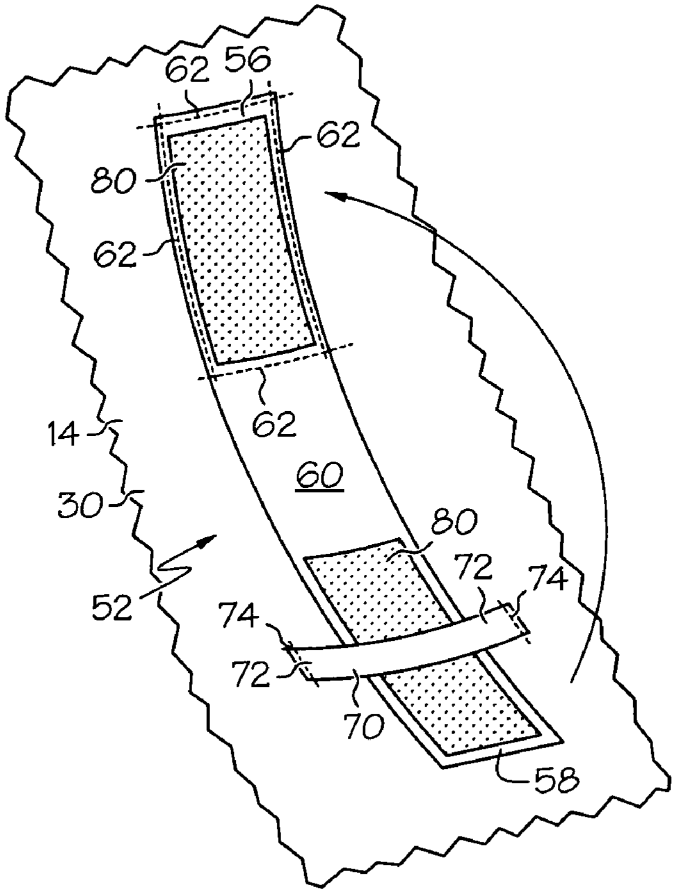
FIG. 4 is a detail perspective view of the adjustable loops of the garment of FIGS. 1 and 3 shown in a release position.
Figure 5:
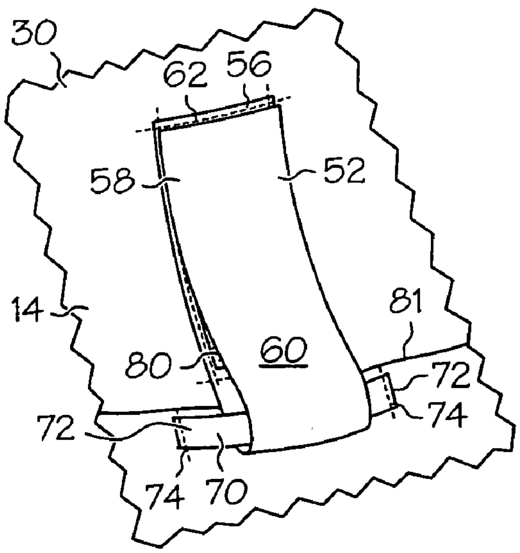
FIG. 5 is a detail perspective view of the loop of FIG. 4, shown in an engaged or drawn-up position.

As shown in FIGS. 4 and 5, each adjusting strip 52 may have a base portion 56 which is fixedly coupled to the outer shell 30, a free end 58 located at the distal end of the adjusting strip 52, and an attachment portion 60 located between the base portion 56 and the free end 58. The base portion 56 may be coupled to the outer shell 30 by a wide variety of mechanisms or means, including stitching 62, adhesives, bonding and the like.

The attachment portion 60 may be directly or indirectly coupled to the outer shell 30. For example, in the embodiment shown in FIGS. 4 and 5, the height adjusting system 50 includes a plurality of retaining loops 70, with each retaining loop being located adjacent to an associated height adjusting strip 52. Each retaining loop 70 may be fixedly coupled to the outer shell 30 and located over the attachment portion 60 of an associated adjusting strip 52 to thereby indirectly couple the associated attachment portion 60 to the outer shell 30. Each retaining loop 70 includes a pair of ends 72, each end 72 being fixedly coupled to the shell 30 on opposite sides of the adjusting strip 52 (i.e., by stitching 74). Each retaining loop 70 is oriented generally perpendicular to the central axis A and generally perpendicular to the adjusting strips 52.

Figure 6:
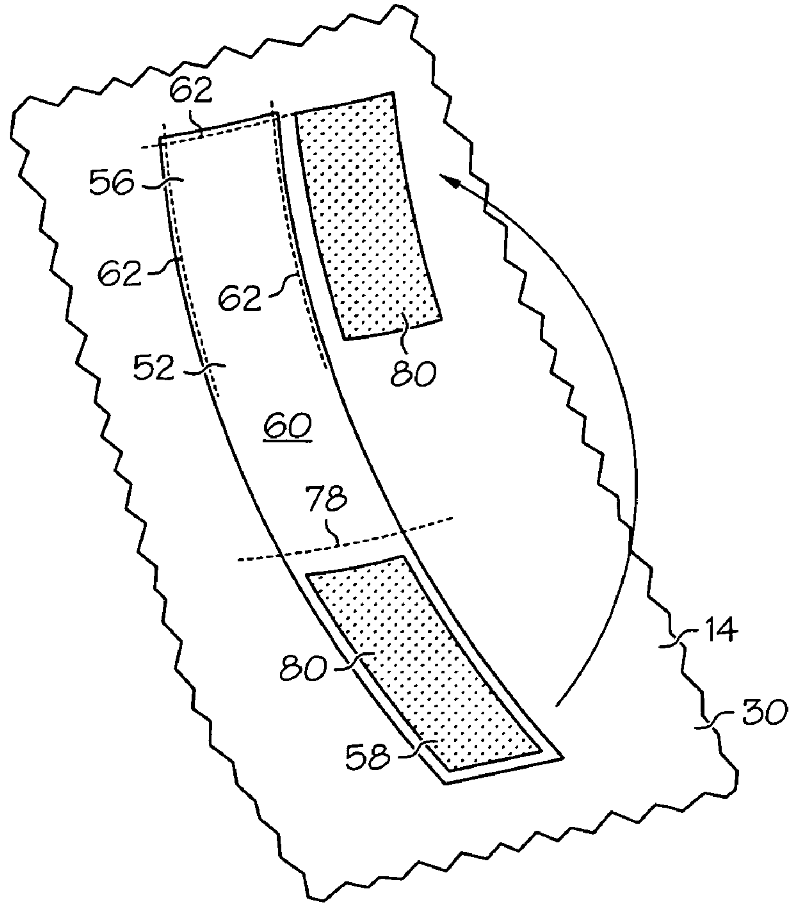
FIG. 6 is a detail perspective view of an alternate embodiment of the adjustable loops of the present invention, shown in a release position.
Figure 7:
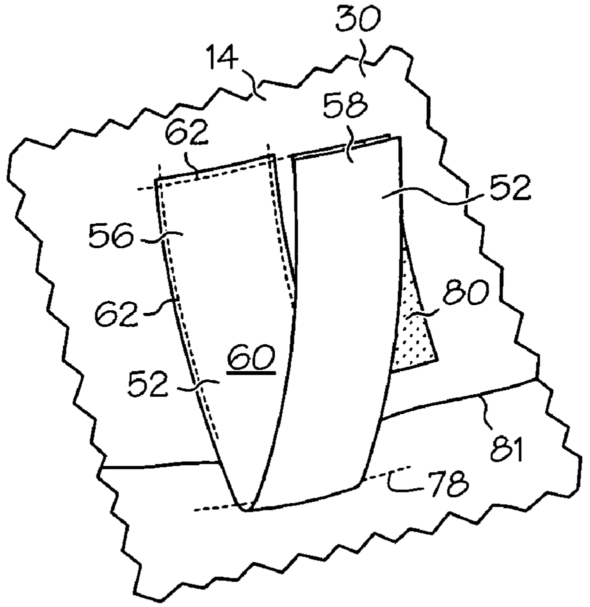
FIG. 7 is a detail perspective view of the loop of FIG. 6, shown in an engaged or drawn-up position.

In an alternate embodiment, rather than being indirectly attached to the outer shell 30 (i.e., by the retaining loop 70), the attachment portion 60 of each adjusting strip 52 may be directly coupled to the outer shell (i.e., by stitching, adhesives, bonding or the like). Thus, FIGS. 6 and 7 illustrate an embodiment wherein the attachment portion 60 is directly coupled to the outer shell 30 by a line of stitching 78. In this embodiment the strips 52 may not need or include the base portion 56 of the strips 52, and may include only the attachment portion 60 and free end. 58. However, use of the retaining loop 70 may increase the leverage when lifting the garment 10 (i.e. reducing its height) and thus improve the ease of use.

The free end 58 and the base portion 56 of each adjusting strip 52 may be releasably attachable together to form the adjusting strip 52 in a generally closed loop. For example, as shown in FIGS. 4 and 5, the base portion 56 and free end 58 both include corresponding patches 80 of hook-and-loop fastening material (such as VELCRO®) that can be pressed together to releasably attach the free end 58 to the base portion 56.

In this manner, as shown in FIG. 5, when the patches 80 are pressed together and the adjusting strip 52 is moved into its generally closed loop shape, the attachment portion 60 pulls the retaining loop 70 generally upwardly. Movement of the retaining loop 70 upwardly pulls the portions of the garment 10 to which the retaining loop 70 is attached generally upwardly to reduce the height of the garment and folds the garment 10 to create fold line 81. As can be seen in a comparison between FIGS. 1 and 3, moving the adjusting strips 52 to their generally closed loop shape reduces the length of the garment 10 so that it can better fit the height of the wearer 20 shown therein.

In an alternate embodiment, instead of locating the upper patch 80 of hook-and-loop fastening material on the base portion 56, a patch 80 of hook-and-loop fastening material may be located on the outer shell 30 (i.e., generally adjacent to the base portion 56) as shown in FIG. 6. In this manner, when the patches 80 of hook-and-loop fastening material are engaged, the adjusting strips 52 are in a generally closed loop shape and pull the lower portion of the garment 10 generally upward to reduce the length (height) of the garment 10.

Thus, the height adjusting system 50 enables the height of the garment 10 to be quickly and easily adjusted. In particular, simply by separating the free end 58 from the base portion 56 of each adjusting strip 52, and reattaching the free end 58 to the base portion 56 at the desired location, the height of the garment 10 can be easily adjusted. Each of the patches 80 of hook-and-loop fastening material may extend along the height of the garment 10 so that the patches 80 can be engaged in a wide variety of configurations (i.e., fully overlapping, various degrees of partially overlapping, etc.) so that the height of the garment 10 can be set to a variety of dimensions. Furthermore, because the free ends 58 can be easily gripped, the height adjusting system 50 can be easily operated by a wearer, even when wearing protective gloves or the like. Finally, the height adjusting system 50 is intuitive and easy to use.

Of course, a wide variety of structures besides the patches 80 of hook-and-loop fastening material may be used to couple the free ends 58 and base portions 56, including but not limited to snaps, clasps, interengaging geometries, cords, ties, zippers, magnets and the like.

Figure 8:
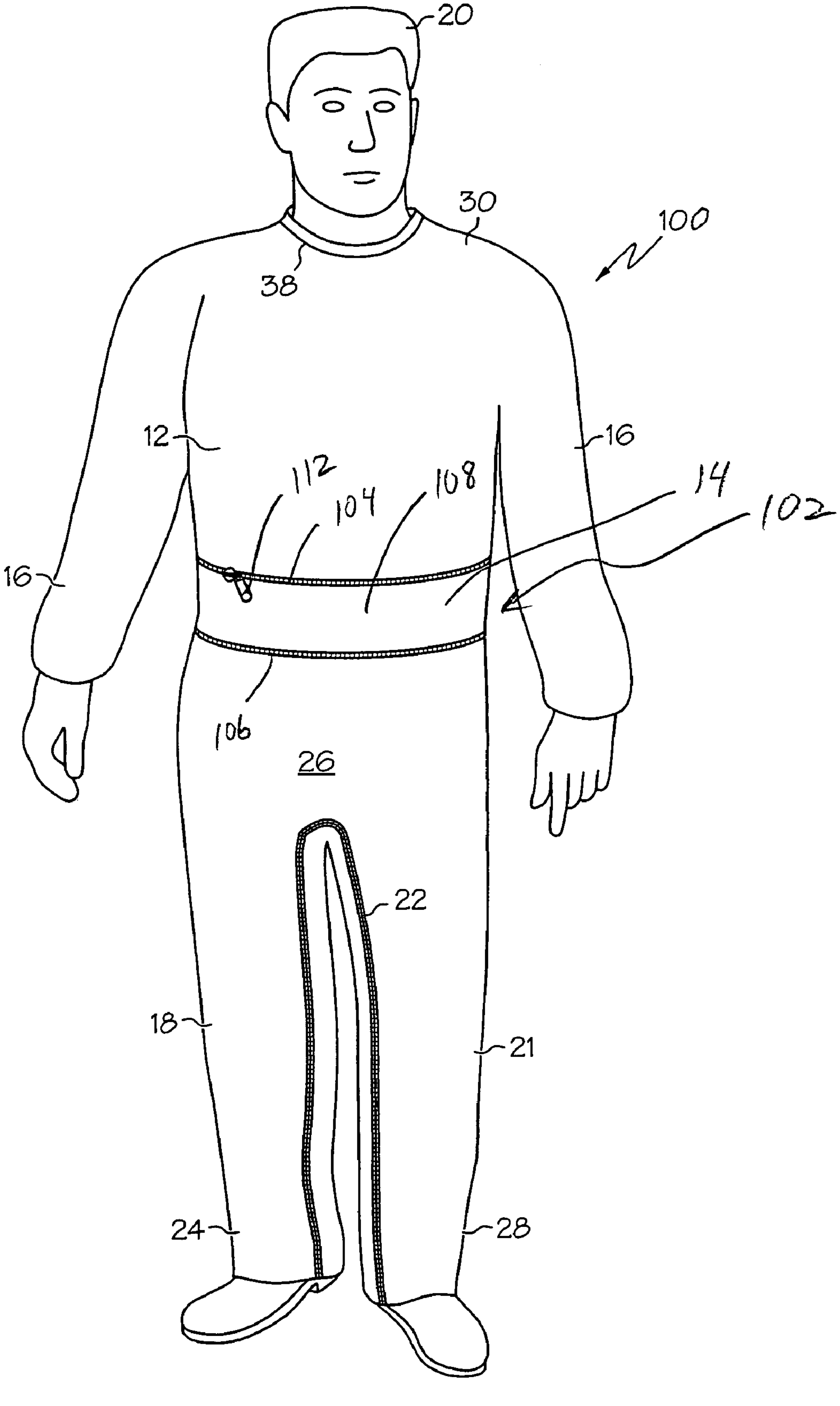
FIG. 8 is a front perspective view of another embodiment of the protective garment of the present invention, shown in a release position.
Figure 9:
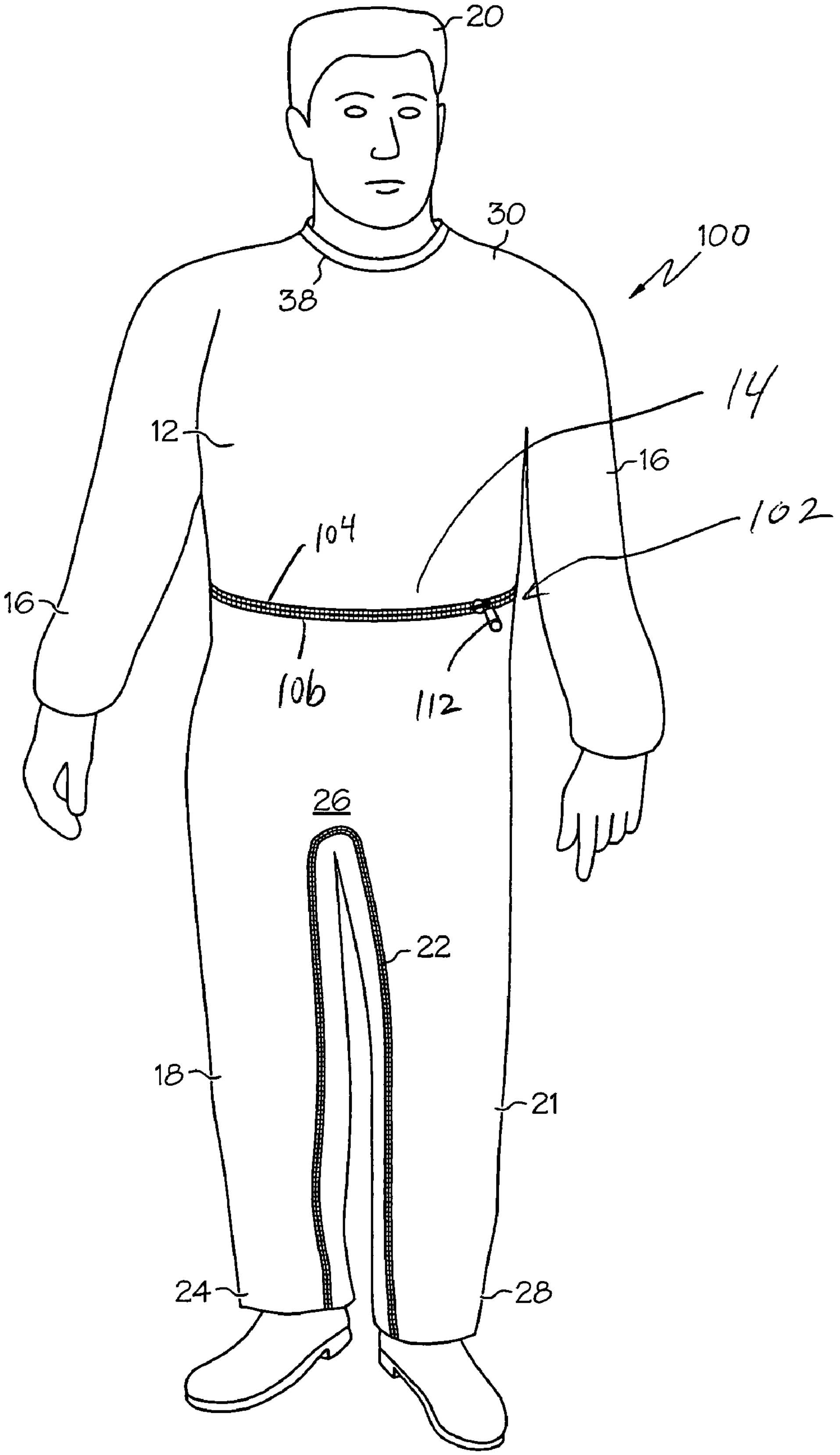
FIG. 9 is a front perspective view of the protective garment of FIG. 1, shown in a drawn-up position.

FIGS. 8–9 illustrate an alternate embodiment of the invention, illustrated as garment 100. The garment 100 includes a height adjusting system 102 which includes first and second attaching strips 104, 106 which are located on and/or coupled to the outer shell 30. Each attaching strip 104, 106 is located at or adjacent to the waist portion 14 and extends around the waist portion 14 to form a generally closed loop shape. In the illustrated embodiment the generally closed loop shape is a circle or oval.

The first and second attaching strips 104, 106 are generally parallel, and in the configuration shown in FIG. 8 are spaced apart such that a strip of intermediate material 108 is located between the attaching strips 104, 106. The first and second attaching strips 104, 106, are releasably attachable together. Thus, the first and second attaching strips 104, 106 may be portions of a zipper, slide fastening system, pieces of hook-and-loop fastening material, or the like. In the embodiment shown in FIGS. 8 and 9, the first and second attaching strips 104, 106 are portions of a zipper which can be releasably coupled by a zipper pull 112. The first and second attaching strips 104, 106 need not necessarily being continuous. For example, when the first and second attaching strips 104, 106 are patches of hook-and-loop fastening material, the first and second attaching strips 104, 106 may extend intermittently around the waist portion 14 of the garment to form a generally closed loop shape.

FIG. 8 illustrates the garment 100 in its release position wherein the garment 100 is relatively long and the height adjusting system 102 is disengaged such that the first and second attaching strips 104, 106 are not coupled together. When it is desired to shorten the length (height) of the garment 100, the height adjusting system 102 is moved to its engaged position by releasably attaching the attaching strips 104, 106. For example, in the embodiment shown in FIG. 8, the portions of the attaching strips 104, 106 located adjacent to the zipper pull 112 are pulled together such that the zipper pull 112 can be operated to zip the attaching strips 104, 106 together. The zipper pull 112 is then passed around the perimeter of the waist portion 14 to couple to attaching strips 104, 106 together, as shown in FIG. 9.

When the garment 100 is moved to its configuration shown in FIG. 9, the strip of intermediate material 108 is folded up and located radially inwardly of the attaching strips 104, 106. When it is desired to return the garment 100 to its longer configuration, the zipper pull 112 is simply moved about the perimeter of the waist portion 14 in the opposite direction to unzip the attaching strips 104, 106. Thus, the height adjusting system 102 provides a quick, convenient, and easy-to-operate system for adjusting the height of the garment 100.

In the embodiment shown in FIGS. 8 and 9, the two attaching strips 104, 106 are completely detachable and are directly coupled together by the zipper pull 112. However, the two attaching strips 104, 106 need not be completely detachable. Instead, the attaching strips 104, 106 may be fixedly coupled together (or located immediately adjacent to each other) at a base location so that even when the zipper is unzipped the attaching strips 104, 106 are coupled together at a base point or location (in the same manner as the zipper of a common pair of pants). This configuration provides for quick and easy closure of the zipper because the attaching strips 104, 106 need not be aligned with the zipper pull 112 prior to closing the zipper. In this case, however, each attaching strips 104, 106 may have some overlap in the radial direction; i.e. may extend greater than 360 degrees around the perimeter of the garment 100. Each attaching strip 104, 106 may have an overlap of several inches (i.e. extend about 400 degrees) to ensure that the height of the garment 100 can be adjusted as required at the base point.

Having described the invention in detail and by reference to the preferred embodiments, it will be apparent that modifications and variations thereof are possible without departing from the scope of the invention.

What is claimed is:

1. A height adjustable protective garment comprising:

an outer shell shaped to fit about and substantially cover the chest, torso and legs of a wearer and having a waist portion shaped to be located at or adjacent to a waist of a wearer wherein said outer shell is abrasion, flame and heat resistant and resists igniting, burning, melting, dripping or separation when exposed to a temperature of 500° F. for at least five minutes; and an adjusting strip having an attachment portion directly or indirectly coupled to said outer shell and a free end which is generally spaced apart from said attachment portion, said free end being releasably attachable to said outer shell or to said adjusting strip to adjust the height of said protective garment, said adjusting strip being located at or adjacent to said waist portion, and wherein said adjusting strip is located on an outer surface of said outer shell such that said adjusting strip can be easily accessed when said outer shell is worn.

2. The garment of claim 1 wherein said adjusting strip includes a base portion fixedly coupled to said outer shell and spaced apart from said attachment portion, and wherein said attachment portion is located between said base portion and said free end.

3. The garment of claim 1 wherein said adjusting strip is shaped and located such that when said free end is releasably attached to said outer shell or to said adjusting strip the attachment portion pulls the portions of said outer shell to which said attachment portion is coupled generally upwardly to reduce the height of said garment.

4. The garment of claim 1 wherein said adjusting strip is formed in a generally closed loop shape when said free end is releasably attached to said outer shell or to said adjusting strip.

5. The garment of claim 4 wherein said adjusting strip is releasably attachable to itself to form said generally closed loop shape.

6. The garment of claim 5 wherein said adjusting strip includes first and second portions of hook and loop fastening material which are releasably attached when said adjusting strip is formed into said generally closed loop shape.

7. The garment of claim 6 wherein said adjusting strip includes a base portion fixedly coupled to said outer shell and spaced apart from said attachment portion, said attachment portion being located between said base portion and said free end, and wherein said first portion of hook and loop fastening material is located on or adjacent to said base portion and wherein said second portion of hook and loop fastening material is located on or adjacent to said free end.

8. The garment of claim 4 wherein said adjusting strip is releasably attachable to said outer shell to form said generally closed loop shape.

9. The garment of claim 8 wherein said garment includes first and second portions of hook and loop fastening material which are releasably attachable to form said adjusting strip into said generally closed loop shape, and wherein said first portion of hook and loop fastening material is located on said outer shell and wherein said second portion of hook and loop fastening material is located on or adjacent to said free end.

10. The garment of claim 4 wherein said adjusting strip is spaced away from a crotch of said garment when said adjusting strip is formed in said generally closed loop.

11. The garment of claim 1 wherein said garment has a central axis extending generally perpendicular to the waist of said garment, and wherein said adjusting strip is oriented generally parallel to said central axis.

12. The garment of claim 1 wherein said outer shell includes a material selected from a group of consisting of an aramid material, a blend of aramid materials, a polybenzamidazole material, and a blend of aramid and polybenzamidazole materials.

13. The garment of claim 1 further comprising a moisture barrier located generally inside of said outer shell such that when said garment is worn said moisture barrier is located generally between said outer shell and a wearer of said garment, said moisture barrier being generally co-extensive with said outer shell and being made of a material that is generally liquid impermeable and generally moisture vapor permeable.

14. The garment of claim 13 wherein said moisture barrier includes expanded polytetrafluoroethylene.

15. The garment of claim 13 further comprising a thermal liner located generally inside said outer shell such that when said garment is worn said thermal liner is located generally between said outer shell and a wearer of said garment.

16. The garment of claim 15 wherein said moisture barrier is generally located between said outer shell and said thermal liner.

17. The garment of claim 15 wherein said thermal liner includes a material selected from a group consisting of an aramid needlepunch material, an aramid batting material, an aramid non-woven material, an aramid-blend needlepunch material, an aramid-blend batting material and an aramid-blend non-woven material.

18. The garment of claim 15 further comprising a face cloth layer located inside of said thermal liner and located to be the innermost layer of said garment.

19. The garment of claim 1 wherein said free end is generally spaced apart from said attachment portion along a length of said adjusting strip.

20. The garment of claim 1 wherein said outer shell includes a front portion and a rear portion, and wherein said attachment portion is located on one of said front or rear portions, and wherein said free end is configured to be releasably attachable to said one of said front or rear portions of said outer shell or to said attachment portion.

21. The garment of claim 1 wherein said adjusting strip is coupled to said outer shell at a base portion and has a length that is less than the distance between said base portion and a crotch of said garment.

22. The garment of claim 1 wherein said outer shell is a one-piece garment and is configured to fit around and substantially cover the arms of a wearer.

23. The garment of claim 1 wherein said outer shell includes a pair of pant legs, each pant leg being shaped and configured to receive a leg of a wearer therethrough.

24. The garment of claim 1 wherein said outer shell includes or defines an inner cavity shaped to receive a wearer therein when said outer shell is configured in a proper orientation, and wherein said outer shell includes an inner surface located adjacent to and defining said inner cavity and wherein said outer surface is positioned on an opposite side of said outer shell relative to said inner cavity.

25. A height adjustable protective garment comprising:

an outer shell shaped to fit about and substantially cover the chest, torso and legs of a wearer and having a waist portion shaped to be located at or adjacent to a waist of a wearer; and an adjusting strip having an attachment portion directly or indirectly coupled to said outer shell and a free end which is generally spaced apart from said attachment portion, said free end being releasably attachable to said outer shell or to said adjusting strip to adjust the height of said protective garment, said adjusting strip being located at or adjacent to said waist portion, and wherein said adjusting strip is located on an outer surface of said outer shell such that said adjusting strip can be easily accessed when said outer shell is worn, said garment having a central axis extending generally perpendicular to the waist of said garment, and wherein said adjusting strip is oriented generally parallel to said central axis, and wherein said adjusting strip includes a base portion fixedly coupled to said outer shell and spaced apart from said attachment portion, and wherein said attachment portion is located between said base portion and said free end, and wherein said adjusting strip further comprises a retaining loop fixedly coupled to said outer shell and located over said attachment portion to indirectly couple said attachment portion to said outer shell.

26. The garment of claim 25 wherein said retaining loop is oriented generally perpendicular to said central axis.

27. The garment of claim 25 wherein said retaining loop has a pair of ends, each end being fixedly coupled to said shell on opposite sides of said adjusting strip.

28. A height adjustable protective garment comprising:

an outer shell shaped to fit about and substantially cover the chest, torso and legs of a wearer and having a waist portion shaped to be located at or adjacent to a waist of a wearer; and an adjusting strip having an attachment portion directly or indirectly coupled to said outer shell and a free end which is generally spaced apart from said attachment portion, said free end being releasably attachable to said outer shell or to said adjusting strip to adjust the height of said protective garment, said adjusting strip being located at or adjacent to said waist portion, and wherein said adjusting strip is located on an outer surface of said outer shell such that said adjusting strip can be easily accessed when said outer shell is worn, wherein said garment includes a plurality of adjusting strips each having a base portion fixedly coupled to said outer shell, an attachment portion directly or indirectly coupled to said outer shell at a location spaced apart from said base portion, and a free end which is generally spaced apart from said attachment portion, said free end of each adjusting strip being releasably attachable to said outer shell or to the associated adjusting strip to adjust the height of said protective garment, and wherein said adjusting strips are spaced about said waist of said garment such that at least one of said plurality of adjusting strips is located on a rear portion of said outer shell and at least one of said plurality of adjusting strips is located on an opposed front portion of said outer shell.

* * * * *

UNITED STATES PATENT AND TRADEMARK OFFICE

CERTIFICATE OF CORRECTION

PATENT NO. : 7,168,103 B2
APPLICATION NO. : 10/749758
DATED : January 30, 2007
INVENTOR(S) : Donald Aldridge et al.

It is certified that error appears in the above-identified patent and that said Letters Patent is hereby corrected as shown below:

On the Title Page Item (73) Assignee

Second Assignee should be -- Government Of The United States, As Represented By The Secretary Of The Navy --.

Claims

Col. 8, Line 4, After "group", delete "of".

Signed and Sealed this

Fifth Day of August, 2008

JON W. DUDAS
*Director of the United States Patent and Trademark Office*